(12) United States Patent
Changaris

(10) Patent No.: US 7,074,418 B2
(45) Date of Patent: Jul. 11, 2006

(54) CONJUGATED FATTY ACID BASED EMULSION AND METHODS FOR PREPARING AND USING SAME

(76) Inventor: David G. Changaris, 801 Barret Ave., Suite 103, Louisville, KY (US) 40204

( * ) Notice: Subject to any disclaimer, the term of this patent is extended or adjusted under 35 U.S.C. 154(b) by 199 days.

(21) Appl. No.: 10/298,405

(22) Filed: Nov. 18, 2002

(65) Prior Publication Data

US 2004/0096468 A1    May 20, 2004

(51) Int. Cl.
*A61K 9/00* (2006.01)
*A61K 6/00* (2006.01)
*A61K 31/19* (2006.01)
*A61K 31/20* (2006.01)
*A61K 31/195* (2006.01)

(52) U.S. Cl. .................. 424/400; 424/401; 514/557; 514/558; 514/561

(58) Field of Classification Search ............... 424/400, 424/401; 514/558, 557, 561
See application file for complete search history.

(56) References Cited

U.S. PATENT DOCUMENTS

| | | | |
|---|---|---|---|
| 4,393,043 A | 7/1983 | Koulbanis et al. | |
| 4,400,295 A | 8/1983 | Ootsu et al. | |
| 4,661,343 A * | 4/1987 | Zabotto et al. | 424/59 |
| 4,732,892 A | 3/1988 | Sarpotdar et al. | |
| 6,162,442 A | 12/2000 | Lotter et al. | |
| 6,162,444 A | 12/2000 | Dubois | |
| 6,245,811 B1 | 6/2001 | Horrobin et al. | |
| 6,287,553 B1 | 9/2001 | Alaluf et al. | |
| 6,290,974 B1 | 9/2001 | Swaisgood et al. | |
| 6,316,030 B1 | 11/2001 | Kropf et al. | |
| 6,420,342 B1 | 7/2002 | Hageman et al. | |
| 2001/0041187 A1 | 11/2001 | Hastings et al. | |
| 2001/0041708 A1 | 11/2001 | Halvorsen et al. | |
| 2002/0013365 A1 | 1/2002 | Fimreite | |
| 2002/0022052 A1 | 2/2002 | Dransfield | |
| 2002/0058071 A1 | 5/2002 | Siskind | |
| 2003/0180277 A1 * | 9/2003 | Hoppe et al. | 424/94.1 |

FOREIGN PATENT DOCUMENTS

| | | | |
|---|---|---|---|
| KR | 2002074443 A | * | 9/2002 |
| WO | WO00/00186 A | * | 1/2000 |
| WO | WO02/09657 A | * | 2/2002 |

* cited by examiner

Primary Examiner—Sreeni Padmanadhan
Assistant Examiner—Marina Lamm
(74) Attorney, Agent, or Firm—Steve A. Witlers; Middleton Reutlinger

(57) ABSTRACT

Stable emulsions comprising as a base one or more diene conjugated fatty acids. Amino acids and other macromolecules can be used to stabilize the emulsion. The emulsion is also useful as a carrier and delivery vehicle of the macromolecules to humans or animals in need of the macromolecules. Plant oil extracts, such as conjugated linoleic acid and its acylated derivatives, are useful as the diene conjugated fatty acids that form the base of the stable emulsion. The emulsions formed are useful as nutritional or cosmetic adjuvant for oral based nutrition, skin diseases, cosmetic utility, enhancing oral nutrition, or pharmacological benefit. Methods of producing and using the emulsions are also provided.

20 Claims, No Drawings

CONJUGATED FATTY ACID BASED EMULSION AND METHODS FOR PREPARING AND USING SAME

FIELD OF THE INVENTION

The present invention relates to a simplified product and method for producing emulsions having a base of diene conjugated fatty acids (CFAs). More specifically, the invention relates to the formation of stable emulsions when oil based solutions of CFAs are admixed with selected macromolecules to form simple mixtures or pastes. The mechanical mixing in of water (water in oil or w/o) to the paste then forms a stable emulsion. Amino acids are particularly useful macromolecules that when admixed with CFA aid in producing the stable emulsions taught by the present invention. Other macromolecules such as DNA, RNA and peptides will similarly form stable emulsions.

BACKGROUND OF THE INVENTION

Lotions or emulsions remain an important component of human concourse. Emulsions act as a vehicle for the injection, enteral, and transdermal incorporation of molecules into man and animal. The utility of an emulsion of 25% oil and 75% water is recognized with its utility including the "feel" of the product. Most plant oils contain approximately 14 g fat and 120 calories per tablespoon. Thus, ordinary lotions deliver 14 grams of fat and 120 calories per ounce. Therefore, emulsions can provide a means of delivering calories to man or animal. In those emulsions approaching 25% oil, there would be half this amount. The equal proportions of oleophilic and hydrophilic substances solubilize in emulsion with humectants and emulsifiers such as cetyl alcohol. The resulting compositions can be used as components of sauces for food, hand moisturizers, cosmetics for the face or as vehicles for delivering chemical compounds to the skin to enhance beauty or treat disease. The various sequencing of mixing oil into water (o/w), water into oil (w/o), and varying mixtures of w/o/w or o/w/o to produce lamellae progressively are part of the general knowledge of emulsions. At the other extreme, oils and waxes contain small amounts of water to form creams and ointments.

As a delivery vehicle, emulsions can be used to construct bi-lipid membranes containing sub-microscopic packages of solutions or artificial liposomes suspended in solution. There is numerous art dealing with liposome preparations of drugs. All of these require high temperatures, high energy mechanical mixing (often times high shear), centrifugation, or settling. It is also known in the art to use CFAs, and more specifically conjugated linoleic acids in emulsions for cosmetic applications. However, such use appears to remain limited to acylated esters or conjugated linoleic acid itself in small concentrations for the effect of intradermal cosmetic goals. These goals can be met with small concentrations of CFA. Other inventions seek specific isomer related effects.

The simplest of emulsions are comprised of 50% oil and water mixtures. However, these are not generally stable over even short time periods and will separate into distinct oil and water layers upon standing. Generally, the process for forming stable emulsions may involve heating, cooling, or mechanical mixing with numerous emulsifiers, such as diethyl amine or cetyl alcohol. For example, stable emulsions generally result from heating equal parts of oil and water with miscing agents heated to 70 degrees centigrade and cooled while mixing. It is generally held in the prior art that formation of stable emulsions at room temperature requires a number of petroleum byproducts. Byproducts from these processes can have deleterious health consequences. For example, it has been estimated that triethylamine (TEA), a commonly used additive, production in the US alone approaches 1.2 billion pounds. Its biological impact remains neutral at best. The reduction of this additive would eliminate one more source of additive related health risks. All of these processes require admixture with various humectants and/or emulsifiers to produce pleasing stable emulsions.

It would be desirable to be able to produce a stable emulsion for use in various applications including, emulsions as vehicles for the injection, enteral, and transdermal incorporation of molecules into man and animal, as lotion bases for dermal applications including moisturizing the skin and for nutrient and calorie delivery without the requirement for complicated and expensive procedures. Additionally, it would be desirable to be able to produce such useful emulsions without the need for added components such as stabilizers and emulsifiers that add expense and may produce toxic byproducts.

SUMMARY OF THE INVENTION

It is accordingly a primary object of the present invention to provide a simplified product and method for producing emulsions having a base of diene conjugated fatty acids (CFAs).

More particularly, it is an object of the present invention to provide stable emulsions formed when oil based solutions of CFAs are admixed with particular macromolecules to form simple mixtures or pastes. The mechanical mixing in of water (water in oil or w/o) to the paste then forms a stable emulsion. Amino acids are particularly useful macromolecules that when admixed with CFA aid in producing the stable emulsions taught by the present invention. Other macromolecule such as DNA, RNA and peptides will similarly form stable emulsions. Also provided are methods of producing these emulsions and methods of use for the emulsions of the present invention.

DETAILED DESCRIPTION OF THE PREFFERED EMBODIMENT

The present invention is based on the discovery that diene conjugated fatty acids (CFAs) are useful in combination with other macromolecules as bases for forming stable emulsions that are easy to produce. The present invention includes methods for producing these emulsions and broadly comprises the steps of 1) combining CFAs with macromolecules such as amino acids, peptides, and/or other amphipathic molecules to form a paste and 2) admixing water with the paste to form an emulsion. Conjugated linoleic acid in one embodiment of the present invention functions superiorly as a CFA base. It has also been discovered that when certain amino acids are used with the base, admixing metal hydroxide solutions with linoleic acid increases the concentration of amino acid that can be solubilized in the emulsion. These emulsions have diverse utilities across the fields of nutrition, pharmacology, therapeutics and manufacturing.

Conjugated fatty acids result from the shift of a double bond in the long chained fatty acid with two double bonds, predominantly in safflower oil and sunflower oil, the diene C18, linoleic acid. The linoleic acid molecule in its natural plant expressed state has two double bonds separated by a single carbon, which is saturated with hydrogen. Thus the molecules C9, C11 and C10, C12 linoleic acids represent two of the most common linoleic acids.

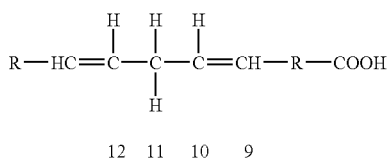

12  11  10  9

This unconjugated form permits the aliphatic and carboxyl ends to rotate around the C10 or C11. This presumably precludes or limits the stability of the amino acid/water complex described herein. The conjugated form derived from alkalinization and extraction has the general formula:

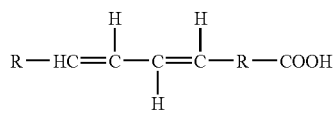

cis- or trans-9, 11 conjugated linoleic acid

In this molecule the center is fixed in a cis or a trans position. The shape resembles a "boomerang" with a hydrophobic center that allows for the orientation of amphipathic molecules and the semi-rigidity of the emulsion. In view of the near total oil incorporation into this process, it is expected that both cis and trans molecules contribute to the process in a stoichiometric fashion.

It is known in the art that fatty acid esters can be bioactive compounds in that they may be capable of delivering acyl groups and fatty acids to cells when ingested orally, administered parenterally, or applied to the skin. However, it was heretofore unknown that emulsions could be formed using CFAs as a base. Quite to the contrary, the prior art specifically identifies that CFAs may be readily emulsified only after the inclusion of galactolipid emulsifiers or phospholipids. Further, it is not known to use amino acids in concert with conjugated fatty acids as an emulsion, as in the present invention.

Long chained fatty acids with diene-conjugated bonds provide a novel and heretofore unrecognized receptor for macromolecule transport, for example amino acids. It is likely that the fixed nature of the central conjugated bonds provide a wedge-shaped site for hydrophobic bonding for lipophilic portions of molecules, aligning the carboxyl terminus with the hydrophilic portion of the molecule allowing for water molecules to aggregate. The observation that metal salts of amino acids with contravening hydroxyl groups on the opposite side suggest that the metal forms weak bonds with the carboxyl terminus which in turn binds the hydrophobic site. This makes fatty acids capable of stabilizing different ends of an amino acid depending on pH, pKa and primary structure of the amino acid or peptide. Acidification of the solution results in immediate loss of emulsion and precipitation of the amino acid within the water phase. This foresees the use of diene-conjugated fatty acids that have receptor-like binding sites that may be used to purify isomers of the diene itself or peptides or amino acids. It should be noted that this emulsion has unique drawbacks with respect to stability. Alcohols, sodium chloride, acidification, alkalinization will destabilize the emulsion.

The conjugated carbon chain of the fatty acid forms a stable platform with these amphipathic molecules and water that protects the integrity of its subcomponents for long-term storage and subsequent purification, ingestion, transdermal delivery, and parenteral administration. Addition of amphipathic lipids such as lecithin and carbomers enhances the stability and generates lamellar o/w/o consistent with liposome formation.

This invention simplifies by reduction the number of chemicals and mechanical steps needed to create a stable emulsion. Furthermore, CFA results from plant oils so there results utility with the discovery that a stable emulsion can be created with conjugated fatty acid isomers admixed with amino acids and water alone and delivered across the skin to be metabolized with the resulting benefit of the conjugated linoleic acid and admixed molecule. That this may have broad reaching social significance results from the follow-on discovery that similar amphipathic molecules such as peptides, DNA, RNA, and ribose also result in emulsions when admixed with CFA.

Each emulsion made with CFA has shown distinct characteristics. First, the use of this process will contribute to a wide range of preparative events. Second, amino acids and essential fatty acids can be stored with reduced degradation at room temperature.

Many of these emulsions are extraordinarily hygroscopic to a point and then no further, others such as proline will incorporate water only while internally supported with a mechanical matrix. For many emulsions heating can cause weeping of the water, but the emulsion resists separation into separate phases to 80 degrees Celsius. Those emulsions with 90% water freeze at temperatures above 0 degrees Celsius and burst to water with mechanical disruption. Alcohols disrupt the emulsion and produce a milky liquid with putative liposomes. Addition of lecithin or use of lipophilic amino acids causes the rejection of oils and therefore provides a simple means to purify the relevant isomers of conjugated fatty acids.

The present invention provides that mixtures of metal hydroxide solutions of amino acids and peptides will form emulsions with conjugated fatty acid preparations that will lend itself to oral ingestion, transdermal, and parenteral injection. Certain amino acids, for example, tryptophan and threonine can be solubilized in high concentration in sodium and potassium hydroxide and stored for long periods at −20 to 0 degrees Celsius.

CFA, acylated CFA and similar molecules will form paste or mechanical mixture with various amino acids and amphipathic molecules that when mixed with water will form stable emulsions for ingestion, transdermal delivery, parenteral administration, storage and purification. High concentrations of amino acids in metal hydroxide solutions can be made into stable emulsions and/or pastes by the simple admixture of conjugated linoleic acid. This results from the conjugated internal R—C=C=C—RCOOH and probably is preserved in other unsaturated long chained fatty acids with similar internal conjugations which may be present to varying degrees in plant oils, and are therefore encompassed by the present invention. Although the prior art identifies conjugated fatty acids as adding qualities to the emulsion but has not identified CFAs as capable of sustaining an emulsion with amino acids per se.

In one embodiment of the present invention, the emulsion comprises CFAs, amino acids and water. The water is preferably found at a concentration of from about 0.01% to about 90% w/v. The CFAs are preferably found at a concentration of between about 0.1% and 70% w/v and more preferably at a concentration of from about 0.1% and 50% w/v. Preferred CFAs include conjugated linoleic acids, for example, 9,11-octadecadienoic acid methyl ester and 10,12-octadecadienoic acid methyl ester. The amino acids are preferably found at a concentration within the emulsion of between about 1% and 70% w/v and more preferably at a concentration of between about 5% and 12% w/v, and even more preferably at a concentration of between about 10% and 12% w/v. Examples of amino acids useful in the emulsion of the present invention include, but are not limited to proline, tyrosine, lysine, phenylalanine, tryptophan, 5-hydroxytryptophan, arginine, glutamine, glycine, methionine, threonine and combinations thereof. The concentration of certain amino acids within the emulsion can be increased by first solubilizing the amino acids in a metal salt solution, for example, a solution of sodium hydroxide or potassium hydroxide.

In another embodiment of the present invention, the emulsion comprises CFAs, one or more macromolecules and water. The water is preferably found at a concentration of from about 30% to about 99.9% w/v. The CFAs and macromolecules are together preferably found at a concentration of between about 0.1% and 70% w/v and more preferably at a concentration of from about 0.1% and 50% w/v and even more preferably from about 0.1% and 40% w/v. Preferred CFAs include conjugated linoleic acids, for example, 9,11-octadecadienoic acid methyl ester and 10,12-octadecadienoic acid methyl ester. The macromolecules found in the emulsion can be, for example, amino acids, deoxyribonucleic acids, ribonucleic acids, carbohydrates and/or peptides. Examples of amino acids useful in the emulsion of the present invention include, but are not limited to proline, tyrosine, lysine, phenylalanine, tryptophan, 5-hydroxytryptophan, arginine, glutamine, glycine, methionine, threonine and combinations thereof. The concentration of certain amino acids within the emulsion can be increased by first solubilizing the amino acids in a metal salt solution, for example, a solution of sodium hydroxide or potassium hydroxide. Examples of preferred carbohydrates useful as macromolecules in the emulsions of the present invention include, but are not limited to, ribose, sucrose and fructose. Examples of preferred peptides useful as macromolecules in the emulsions of the present invention include, but are not limited to glutathione, aspartame, met-enkephalin and leu-enkephalin.

One of the greatest advantages of the emulsions of the present invention over those of the prior art is the simplicity of its composition and relative ease of manufacturing. For example, in one embodiment, an emulsion is formed by simply mechanically mixing together CFAs, a macromolecule of choice, as described above, and water. Alternatively, the CFAs and macromolecules, for example amino acids, can first be admixed to form a paste and then water admixed to the paste to form an emulsion. The emulsions formed according to these methods and with these ingredients as disclosed above are stable and do not separate into phases for extended periods of time in a variety of environmental conditions. Unlike the prior art, the emulsions of the present invention do not require exotic or complicated manufacturing conditions. Further, producing the emulsions of the present invention does not require additional ingredients, such as emulsifiers or other vehicles or carriers that can add both expense and risk to the final product.

As previously stated, the emulsions of the present invention have far ranging applications across the fields of nutrition, pharmacology, therapeutics and manufacturing. For example, the CFAs provide a base that facilitates the delivery of macromolecules intradermally to the skin so as to provide nutrients, calories or hydration to the skin of humans or animals in need of the macromolecules. The CFAs not only provide a carrier base, but they themselves provide essential nutrition to the skin. One method of providing macromolecules, such as those described above, or CFAs intradermally to the skin comprises applying one of the emulsions of the present invention, such as in the form of a lotion, to the skin and then allowing the emulsion to transfer into the skin. In another application of the emulsions of the present invention, it is also possible to use the emulsion to transdermally or transmucosally deliver macromolecules or CFAs through the skin and into the body of a human or animal in need of a particular macromolecule. One method of transdermally or transmucosally delivering a macromolecule, such as those discussed above, into the body of a human or animal comprises applying one of the emulsions of the present invention to the skin or mucous membranes of a human or animal and allowing the emulsion to transfer across the skin or membrane into the body.

In order that the present invention may be more readily understood, the following examples are given, by way of illustration.

EXAMPLES

Example 1

50 mL of CFAs in the form of Tonalin (70% conjugated linoleic acid) are mechanically mixed at room temperature with 5 g hydroxyproline to form a paste. 40 mL of water is added to the paste and mechanically mixed gently at room temperature to form a stable emulsion.

Example 2

50 mL of CFAs in the form of Tonalin (70% conjugated linoleic acid) are mechanically mixed at room temperature with 5 mL of 50 g % tryptophan solubilized in sodium hydroxide to form a paste. 40 mL of water is added to the paste and mechanically mixed gently at room temperature to form a stable emulsion.

The procedures of Examples 1 and 2 were repeated with the following concentrations and reagents:

Example 3

50 mL of CFAs in the form of Tonalin (70% conjugated linoleic acid),

70% by weight tryptophan solubilized in sodium hydroxide(50% tryptophan by weight), and 40 mL water.

Example 4

50 mL of CFAs in the form of Tonalin (70% conjugated linoleic acid),

55% by weight tryptophan solubilized in potassium hydroxide, and 40 mL water.

Example 5

50 mL of CFAs in the form of Tonalin (70% conjugated linoleic acid),

55% by weight threonine solubilized in sodium hydroxide, and 40 mL water.

Example 6

50 mL of CFAs in the form of Tonalin (70% conjugated linoleic acid),
45% by weight threonine solubilized in sodium hydroxide, and
40 mL water.

Example 7

0 mL of CFAs in the form of Tonalin (70% conjugated linoleic acid),
30% by weight tryptophan solubilized in sodium hydroxide, and
40 mL water.

Example 8

50 mL of CFAs in the form of Tonalin (70% conjugated linoleic acid),
35% by weight methionine solubilized in sodium hydroxide, and
40 mL water.

All of the Examples 1–8 resulted in stable emulsions, each having extended shelf lives or were easily reconstituted with gentle shaking, wherein the constituents remained homogenous and remained chemically stable, specifically they did not separate into distinct phases. None of the emulsions exhibited crystal formation. In use, each emulsion of the above examples provided a pleasant texture and absorbed well into the skin upon application, providing excellent hydration.

I claim:

1. An emulsion, consisting of: from about 0.1–50% w/v of a conjugated diene fatty acid; from about 1–70% w/v of one or more amino acids; and from about 0.01–90% w/v of water.

2. The emulsion of claim 1, wherein said conjugated diene fatty acid is conjugated linoleic acid.

3. The emulsion of claim 2, wherein said conjugated linoleic acid is selected from the group of isomers consisting of 9,11-octadecadienoic acid methyl ester and 10,12-octadecadienoic acid methyl ester.

4. The emulsion of claim 1, wherein said one or more amino acids are selected from the group consisting of proline, tyrosine, lysine, phenylalanine, tryptophan, 5 hydroxytryptophan, arginine, glutamine, glycine, methionine, threonine and combinations thereof.

5. The emulsion of claim 1, wherein said amino acids are at a range from about 5–12% w/v.

6. The emulsion of claim 5, wherein said amino acids are at a range of from about 10–12% w/v.

7. The emulsion of claim 4, wherein said one or more amino acids is proline.

8. The emulsion of claim 4, wherein said one or more amino acids are solubilized in a solution containing a metal salt.

9. The emulsion of claim 1, wherein said one or more amino acids are solubilized in a solution containing sodium hydroxide or potassium hydroxide.

10. The emulsion of claim 8, wherein said amino acids are at a concentration of between about 1–35% w/v.

11. An emulsion, consisting of: from about 0.1–70% w/v of a mixture of one or more conjugated diene fatty acids and one or more amino acids; and from about 30–99.9% w/v of water.

12. The emulsion of claim 11, wherein said one or more amino acids are selected from the group consisting of proline, threonine, tyrosine, lysine, phenylalanine, tryptophan, 5 hydroxytryptophan, arginine, glutamine, glycine, methionine, threonine and combinations thereof.

13. The emulsion of claim 12, wherein said one or more amino acids is proline and said mixture is from about 0.1–50% w/v.

14. The emulsion of claim 12, wherein said amino acid is methionine and said mixture is from about 0.1–40% w/v.

15. The emulsion of claim 11, wherein said conjugated diene fatty acid is conjugated linoleic acid.

16. The emulsion of claim 15, wherein said conjugated linoleic acid is selected from the group of isomers consisting of 9,11-octadecadienoic acid methyl ester and 10,12-octadecadienoic acid methyl ester.

17. A method of making an emulsion consisting essentially of mechanically mixing together from about 0.1–70% w/v of a mixture consisting of a conjugated diene fatty acid and one or more amino acids and from about 30–99.9% w/v of water.

18. The method of claim 17, wherein said one or more amino acids are selected from the group consisting of proline, tyrosine, lysine, phenylalanine, tryptophan, 5 hydroxytryptophan, arginine, glutamine, glycine, methionine, threonine and combinations thereof.

19. The method of claim 17, wherein said conjugated diene fatty acid is conjugated linoleic acid.

20. The method of claim 19, wherein said conjugated linoleic acid is selected from the group of isomers consisting of 9,11-octadecadienoic acid methyl ester and 10,12-octadecadienoic acid methyl ester.

* * * * *